US006217598B1

(12) United States Patent
Berman et al.

(10) Patent No.: US 6,217,598 B1
(45) Date of Patent: Apr. 17, 2001

(54) END-CUTTING SHAVER BLADE

(75) Inventors: Phillip J. Berman, Clearwater; Robert A. Van Wyk, Largo, both of FL (US)

(73) Assignee: Linvatec Corporation, Largo, FL (US)

( * ) Notice: Subject to any disclaimer, the term of this patent is extended or adjusted under 35 U.S.C. 154(b) by 0 days.

(21) Appl. No.: 09/193,899

(22) Filed: Nov. 18, 1998

Related U.S. Application Data (60) Provisional application No. 60/069,309, filed on Nov. 25, 1997.

(51) Int. Cl.[7] ................................................ A61B 17/32
(52) U.S. Cl. .............................. 606/167; 606/170
(58) Field of Search ................................ 606/170, 167, 606/22, 42, 23, 180; 128/898, 305; 30/229, 330, 336, 338

(56) References Cited

U.S. PATENT DOCUMENTS

| 4,646,738 | * | 3/1987 | Trott | 128/305 |
| 5,883,294 | * | 1/1999 | Alden | 606/167 |
| 6,001,116 | * | 12/1999 | Heisler et al. | 606/180 |
| 6,053,928 | * | 4/2000 | Van Wyk et al. | 606/167 |

* cited by examiner

Primary Examiner—Henry J. Recla
Assistant Examiner—Anthony S. King
(74) Attorney, Agent, or Firm—Gene Warzecha (57) ABSTRACT

A rotary shaver blade assembly having a laterally facing and end facing cutting window enabling it to resect tissue presented end-wise or at relatively small angles. The assembly is provided with a stationary elongated outer tube and a rotatable inner tube, both having laterally facing and end facing cutting windows and both having planar transverse end walls at their distal tips. The transverse end walls are abutting and are sharpened into edges by being tapered in opposite directions. The end wall of the outer tube is tapered into a concave surface to allow the inner and outer transverse edges to be situated close to target tissue. The edge on the end wall of the inner tube is transversely arcuate and has a point at each end to enable it, in cooperation with the outer edge, to resect tissue presented axially or at shallow angles to the axis of the shaver blade. A method for producing such a shaver blade assembly comprises the formation of intersecting arcuate surfaces to create the various aforementioned edges.

9 Claims, 9 Drawing Sheets

END-CUTTING SHAVER BLADE

This application claims benefit of Provisional No. 60/069,309 filed Nov. 25, 1997.

BACKGROUND OF THE INVENTION

1. Field of the Invention

The invention relates to elongated, powered surgical instruments for use in endoscopic tissue resection. More particularly, the invention relates to an instrument having an elongated inner tube rotatably situated within an elongated stationary outer tube, both inner and outer tubes having, at their distal ends, cutting apertures which cooperate to resect or otherwise affect tissue during endoscopic surgical procedures. Still more particularly, the invention relates to an instrument and the method of manufacturing an instrument in which the cutting apertures at the distal ends of the elongated tubular members of a rotatable surgical instrument are shaped to enhance end-cutting.

2. Description of the Prior Art

The use of elongated surgical cutting instruments has become well accepted in performing closed surgery such as arthroscopic or, more generally, endoscopic surgery. In closed surgery, access to the surgical site is gained via one or more portals, and instruments used in the surgical procedure must be elongated to permit the distal ends of the instruments to reach the surgical site. Surgical cutting instruments for use in closed surgery—also known as "shavers"—conventionally have a straight, elongated outer tubular member terminating at a distal end having an opening in the end or side wall (or both) to form a cutting port or window and a straight, elongated inner tubular member concentrically disposed in the outer tubular member and having a distal end disposed adjacent the opening in the distal end of the outer tubular member. The distal end of the inner tubular member has a surface or edge for engaging tissue via the opening in the outer tubular member and in many cases (but not all) cooperates with the opening to shear, cut or trim tissue. In some cases, such as burrs, the opening in the outer tube merely allows access to the tissue and does not otherwise cooperate to resect tissue. The inner tubular member is rotatably driven about its axis from its proximal end, normally via a handpiece having a small electric motor which is controlled by finger actuated switches on the handpiece, a foot switch or switches on a console supplying power to the handpiece. The distal end of the inner tubular member can have various configurations depending upon the surgical procedure to be performed, and the opening in the distal end of the outer tubular member has a configuration to cooperate with the particular configuration of the distal end of the inner tubular member. For example, the inner and outer tubular members can be configured to produce whisker cutting, synovial resection, arthroplasty burring or abrading, side cutting, meniscus cutting, trimming, full radius resection, end cutting and the like, and the various configurations are referred to generically as shaver blades. Cut tissue is aspirated through the hollow lumen of the inner tubular member to be collected via a vacuum tube communicating with the handpiece.

The aforementioned elongated surgical cutting instruments have also been produced in angled configurations in which the distal tips of the inner and outer members are aligned and offset or bent at either a fixed or variable angle from the proximal ends of the aligned inner and outer members. Examples of fixed and variable angle rotary surgical instruments are shown in U.S. Pat. Nos. 4,646,738 (Trott) and 5,411,514 (Fucci et al.), both assigned to the assignee hereof, and incorporated by reference herein. In other respects the operation of fixed and variable angle shavers is largely the same as that of the straight shavers described above.

One parameter affecting the efficiency of operation of shaver blades is sharpness of the edges of the windows. Various prior art designs are known to have differing degrees of sharpness of both the inner cutting edges and the periphery of the outer window. Additionally, end-cutting applications require that the blades be capable of cutting tissue presented axially or substantially axially. The present invention is concerned with the design and manufacture of an outer tubular member having not only a sharpened window periphery in a lateral direction, but also a sharpened end-facing structure.

General purpose shaver blades (sometimes known as microdebriders) have outer tubes formed by rolling over the end of the tube so that it forms a hemispherical radius. The inner tube is similarly shaped. When cutting edges are formed on the inner and outer tubes the geometry produced is most efficient for resection of tissue presented laterally. Because of the hemispherical distal end shape, the cutting edges are not as efficient in engaging tissue when it is presented axially or at shallow angles to the tube axis.

Special purpose end-cutting shaver blades have been produced in an attempt to overcome this limitation. These differ from the aforementioned blades in that the distal end of the outer tube is not hemispherical but rather is formed with a much smaller radius so as to produce a relatively flat distal surface perpendicular to the axes of the elongated inner and outer tubular members. The cutting window at the distal end of the outer member has both end-facing and lateral-facing portions and the cutting window at the distal end of the inner member has a periphery adapted to grab tissue presented end-wise between the end-facing cooperating teeth or edges of the inner and outer members. While effective for certain tissue, prior art designs have proven ineffective for other tissue such as, for example, ethmoid bone encountered in various ENT (ear-nose-throat) procedures. Prior art end cutters are known which have the diameter of this flat distal surface equal to approximately 70% of the diameter of the body of the outer tube. The flat, end-facing surface is not equal to the tube diameter because the circumferential junction at the transition between the flat distal surface and the cylindrical wall of the outer tubular member has a radius. This radius and the flat nature of the distal surface limit the ability of prior art end-cutting shaver blades to get close (axially) to relatively flat tissue surfaces (such as bone or other firm tissue). The effectiveness of these cutters is also compromised for shallow angle resection. Additionally, the cutting edge geometries of these blades are such that only the distal tip area has low included angle cutting edges. This makes the blades inefficient for side cutting and susceptible to clogging due to tissue wrap.

It is known that improved resection efficiency is achieved by sharpening the cutting edges and this is true of conventional scissors as well as endoscopic shavers although the manufacture of the latter is considerably more difficult. The smaller the included angle of the cutting edge, the sharper the edge. Clearly, below a certain limit the edge becomes too delicate to be practical. When applied to the tubular members of cylindrical, rotating shavers, the cutting window on the inner member and the cutting window on the outer member each have peripheries which are the cooperating edges which rotate cyclically past each other and which should have the smallest included angles in order to produce sharp edges for most efficient resection. U.S. Pat. No. 5,693,063 (VanWyk et al.), assigned to the assignee hereof and incorporated by reference herein, discloses new shaver blade designs and technology which can be incorporated into the invention claimed herein to overcome the disadvantages of prior art end cutters. This technology not only enables production of sharper edges, but also enables the edges to be placed closer to target tissue by minimizing the thickness of the window perimeter.

It is accordingly an object of this invention to produce a shaver blade assembly in which the windows of the inner and outer members have a sharpened periphery.

It is also an object of this invention to produce an end-cutting shaver blade assembly having an outer member with a sharpened, end-facing window formed by a peripheral land surface angled to the window rim.

It is another object of this invention to produce a sharpened outer window of an end-cutting shaver blade with a simple process minimizing the use of complex tools and the number of required processing steps.

It is yet another object of this invention to produce an end-cutting shaver blade capable of getting closer to tissue presented end-wise than prior art end-cutting shavers.

SUMMARY OF THE INVENTION

These and other objects of this invention are achieved by the preferred embodiment disclosed herein which is a shaver blade assembly in the form of an end cutter in which the outer tube distal end is closed by securing (such as by welding) a flat transverse end wall onto the open end of the tube. This essentially eliminates or at least greatly reduces the radius present at the junction of the transverse end wall and cylindrical side wall on formed tubes and results in a cylindrical type rim shape at the distal end. The inner tube distal tip is similarly cylindrically shaped with a transverse end wall. The inner tube cutting edges are formed by a wire and "sinker" EDM (electrical discharge machining) process in such a manner that a sharp corner "tooth" is produced. The outer tube cutting edges are formed by a two-stage electrochemical grinding (ECG) operation in a manner to produce extremely sharp, low included angle cutting edges around the entire window periphery. The combination of a sharp corner "tooth" on the inner cutting edge, and the sharp outer cutting edges on the end face produces a shaver which is able to cut efficiently even when the axis of the shaver is perpendicular to the target tissue or at a shallow angle relative to the tissue surface.

The invention also resides in the method of forming the aforementioned shaver blade assembly using a grinding or electrochemical grinding process described in the aforementioned U.S. Pat. No. 5,693,063. The process is modified, however, in that the cutting window of the outer tubular member is produced in a two-stage process. The first stage comprises orienting the outer tube in a certain orientation to produce the laterally facing portion of the window. The second stage comprises orienting the tube in a different orientation to produce the end-facing portion of the window intersecting with the laterally facing portion.

DESCRIPTION OF THE PREFERRED EMBODIMENT

Figure 1:
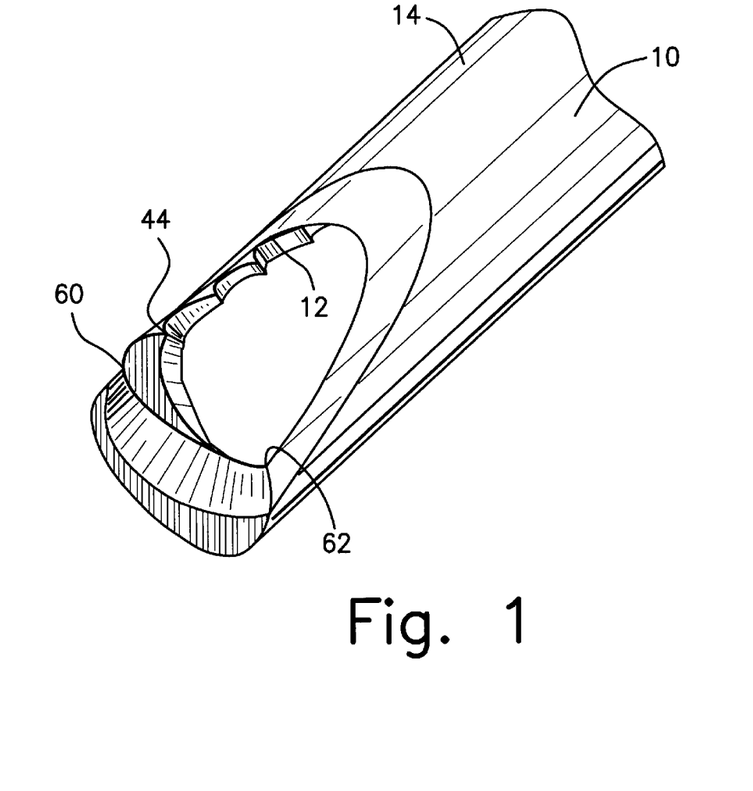
FIG. 1 is a front perspective view of a distal tip of an end-cutting shaver blade formed in accordance with the principles of this invention.
Figure 2:
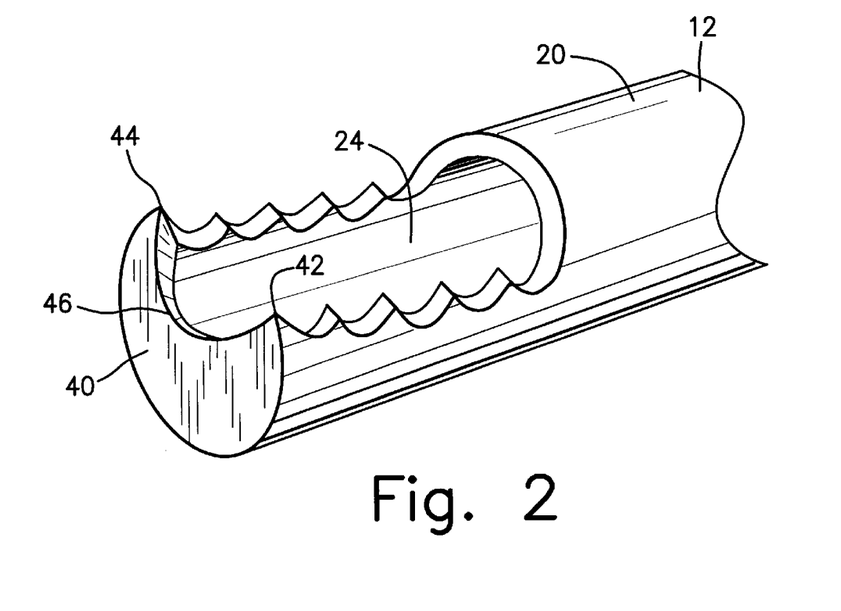
FIG. 2 is a front perspective view of the inner member of the shaver blade shown in FIG. 1.
Figure 3:
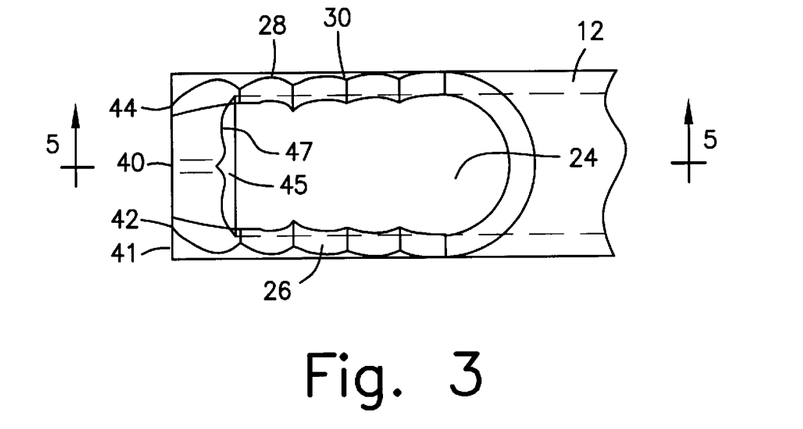
FIG. 3 is a top plan view of FIG. 2.
Figure 4:
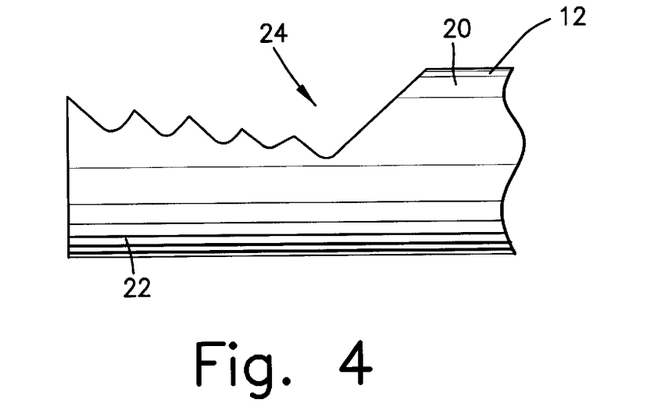
FIG. 4 is a side elevational view of FIG. 3.
Figure 5:
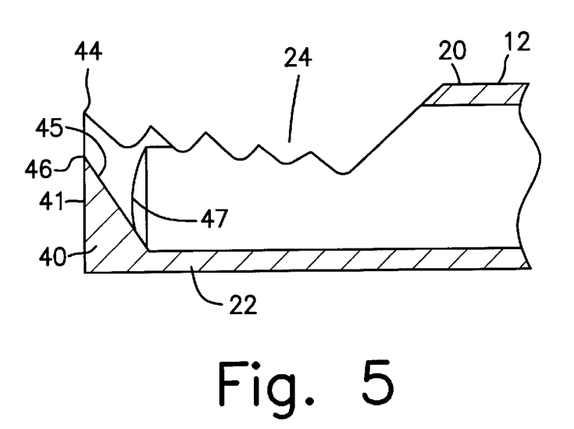
FIG. 5 is a cross-sectional view of FIG. 3 taken along the line 5—5.
Figure 6:
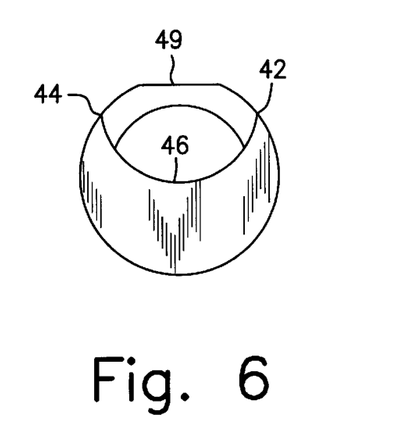
FIG. 6 is an end view of FIG. 5.
Figure 7:
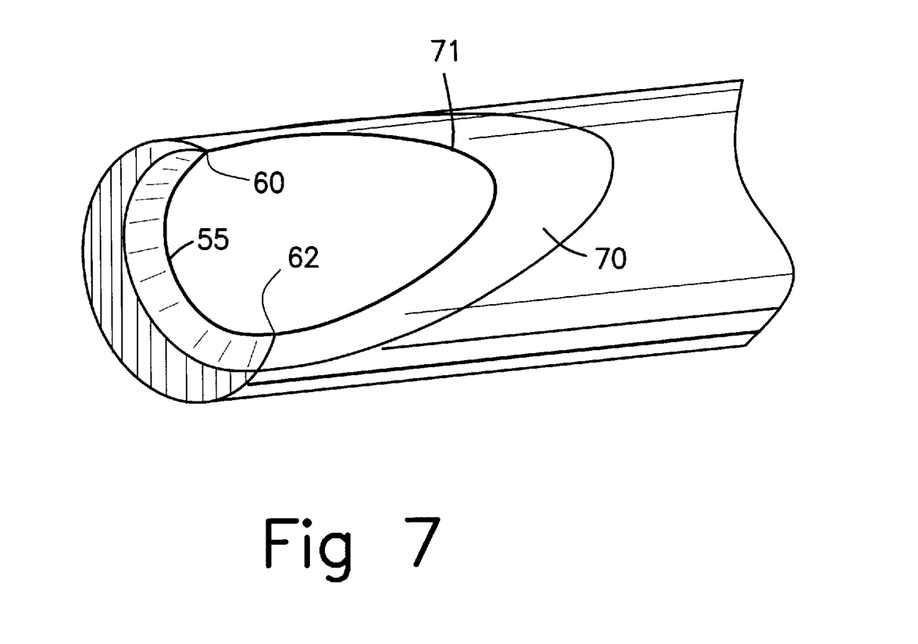
FIG. 7 is a front perspective view of the outer member of the shaver blade shown in FIG. 1.
Figure 8:
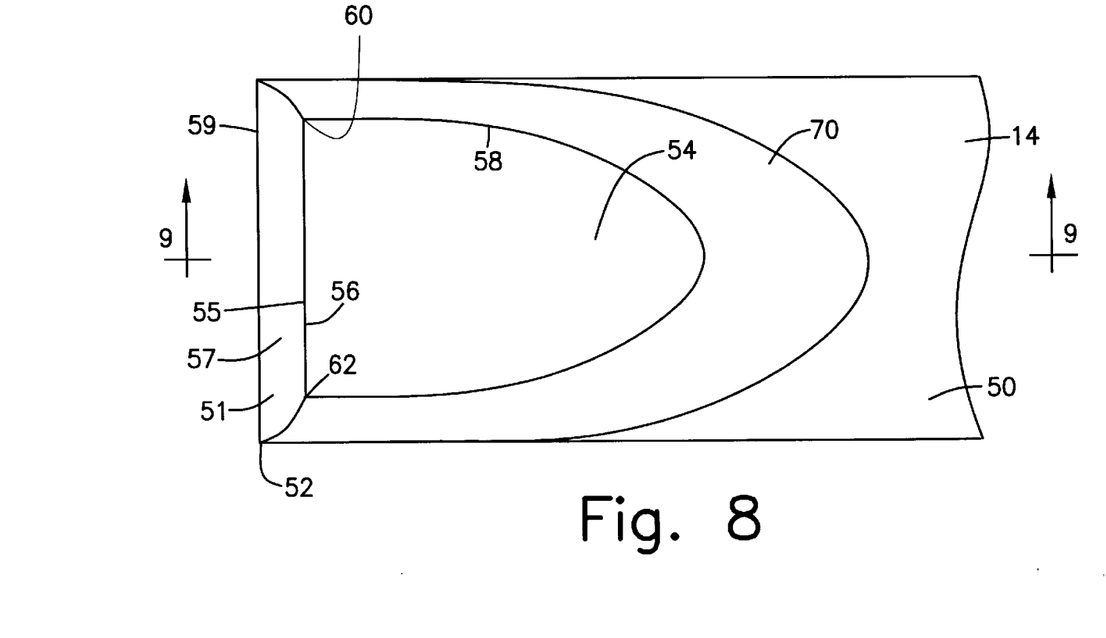
FIG. 8 is a top plan view of FIG. 7.
Figure 9:
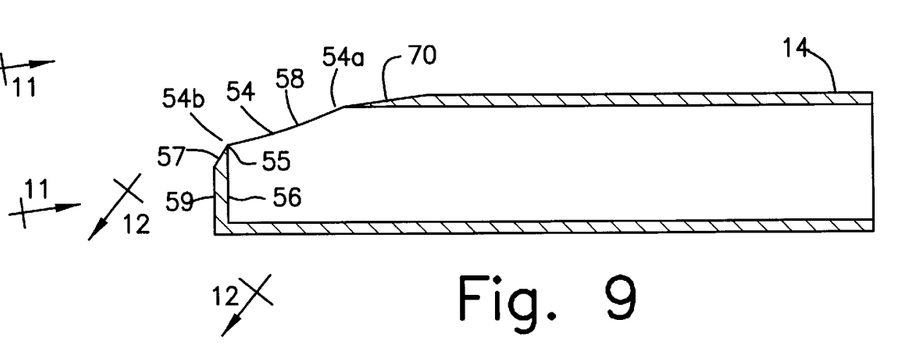
FIG. 9 is a cross-sectional view of FIG. 8 taken along the line 9—9.
Figure 10:
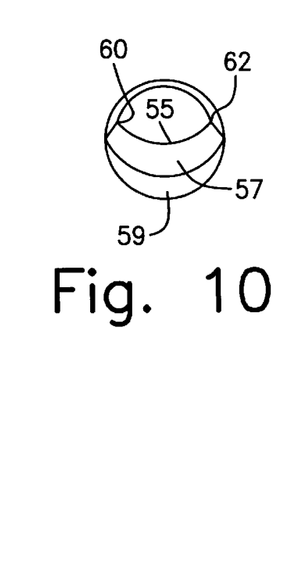
FIG. 10 is an end view of FIG. 9.

Referring to the drawings, FIG. 1 shows a front perspective view of a shaver blade 10 constructed in accordance with the principles of this invention comprising an elongated rotatable inner member 12 situated within a non-rotatable elongated outer member 14. The proximal ends of the tubular member are adapted to be operatively secured to a powered handpiece for rotatably driving the inner member relative to the outer member. These proximal ends are conventional and well understood by those skilled in the art.

Inner member 12, best seen in FIGS. 2 through 6, comprises a cylindrical body 20 which has a distal end 22 shaped to form a cutting window 24 bounded on its two lateral sides by rows 26 and 28 comprising a plurality of teeth 30. It will be understood that the cutting window may alternatively be bounded by a straight or arcuate edge (at the intersection of the inner surface of the inner member and the window) rather than by teeth. The cutting window of the inner member cooperates with the cutting window of the outer member, described below, to resect tissue presented in the opening when the two windows are aligned. The distal tip of inner member 12 is provided with a transverse planar end wall 40 which is flat on its distally facing side 41, tapered at 45 on its proximally facing inner surface 47 and which joins distal-most teeth 42 and 44 situated respectively at each end of arcuate transverse edge 46. The term "facing" as used herein means that the stated element is visible when viewed from the stated direction. For example, an end facing window (or side, etc.) is visible to an observer looking at the window (or side, etc.) from the end of the tubular member. It will be understood that edge 46 could be straight rather than arcuate and could be produced without one or both teeth 42 and 44. While in the preferred embodiment edge 46 is essentially a portion of a circle, numerous other profiles could be suitable.

Inner member 12 is formed from a cylindrical tube having a flat transverse distal surface. This may be accomplished by a circular end cap laser welded along its periphery to the distal open end of a cylindrical tube. Alternatively, the distal end of the tubular member could comprise a machined shell having a cylindrical wall with one closed, flat end and an open end which is welded to the cylindrical tube. Such a process enables the distal end of the tube to be closed by a planar end wall which intersects with the cylindrical surface of the tube at a rim which has a sharper edge, i.e. much smaller radius of curvature than prior art devices. When viewed in an axial plane, the cylindrical and planar surfaces intersect at substantially a right angle along the rim (except, of course, where the cutting window exists). Teeth 30 are formed by a wire EDM process and tapered surface 45 is formed by a sinker EDM. A flat irrigating channel 49 may optionally be formed in the outer surface of member 12 to communicate fluid to its distal end.

Outer tubular member 14 is best seen in FIGS. 8 through 12 and comprises a cylindrical body 50 having a distal end 52 and a cutting window 54. Window 54 has laterally facing and end facing portions 54a and 54b, respectively, as will be understood below. The distal tip of end 52 is provided with a transverse end wall 51 which is flat on its proximally facing surface 56 and preferably has a tapered or concave portion 57 on at least a part of its distally facing surface 59, as will be understood below. The flat and concave, inner and outer surfaces 56 and 57, respectively, meet to form an arcuate transverse edge 55. The intersection of tapered surface 57 and the longitudinally extending part of perimetral cutting edge 58 surrounding window 54 produces distal cutting points 60 and 62. (To the extent edge 58 is defined as the perimeter of window 54, edge 58 includes transverse edge 55.)

Figure 11:
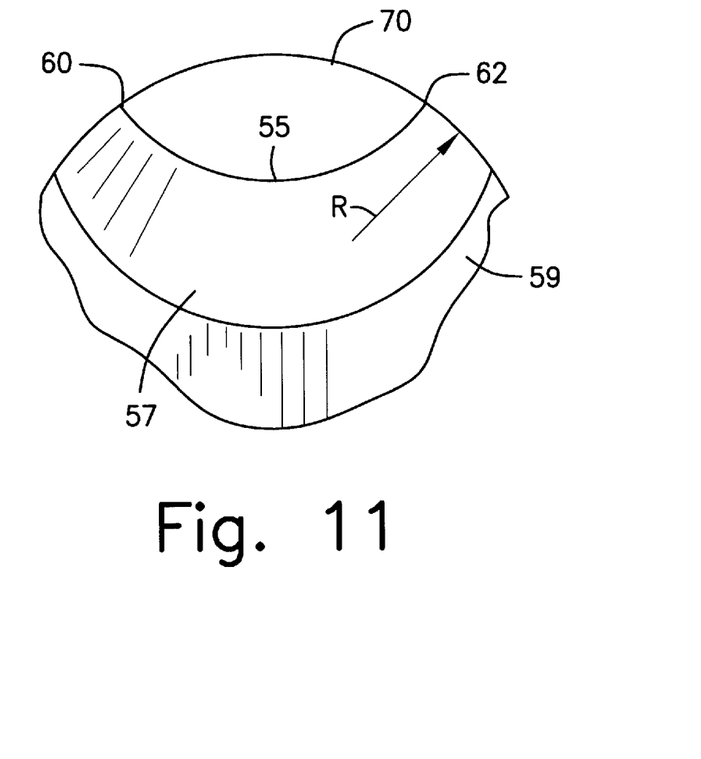
FIG. 11 is a view of FIG. 9 taken along the line 11—11.
Figure 12:
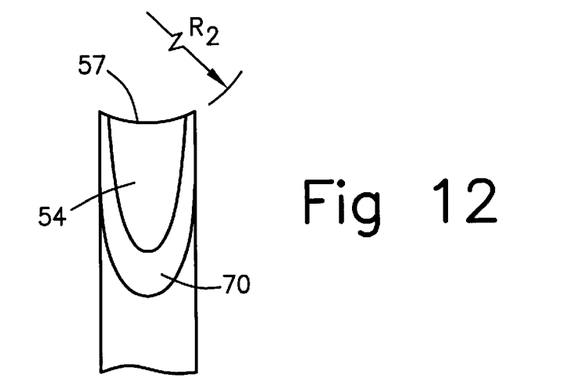
FIG. 12 is a view of FIG. 9 taken along the line 12—12.

Window 54 is essentially the combination of a primarily laterally facing window portion 54a and an end facing window portion 54b. As a result of the process by which outer tubular member is formed, the land 70 surrounding the perimetral cutting edge 58 along its lateral and proximal sides (proximal to points 60 and 62) is an arcuate surface created by the intersection of an arcuate tool with the cylindrical body of outer tube 14. Thus, as best seen in FIG. 11, this land 70 has a predetermined radius of curvature R when viewed endwise along the line 11—11 of FIG. 9. Additionally, arcuate surface 57 on the distal side of end wall 51 of outer tube 14 is formed by the intersection of the tube with a convex cutting tool having a radius of curvature $R_2$ as best seen in FIG. 12 which is a view taken along the line 12—12 of FIG. 9. Referring to FIG. 1, as the inner tube rotates or oscillates within outer tube 14 the tips of the distal-most teeth 42 and 44 pass in scissor-like fashion near cutting points 60 and 62. The structure of blade 10 enables target tissue to be received within the concavity of surface 57 and between the open space between distal most teeth 42 and 44 and points 60 and 62, thus enabling the blade to efficiently resect tissue presented in this space.

In the preferred embodiment, outer cutting window 54 is produced by an electrochemical grinding process described in the aforementioned U.S. Pat. No. 5,693,063 (VanWyk et al.) as modified by the method further explained below with reference to FIGS. 13 through 22. As used herein, the terms "forming" and/or "shaping" an opening or a tube are used interchangeably to refer to the process of producing a shaver blade assembly having the unique distal end structure described herein.

Figures 13, 14, 15:
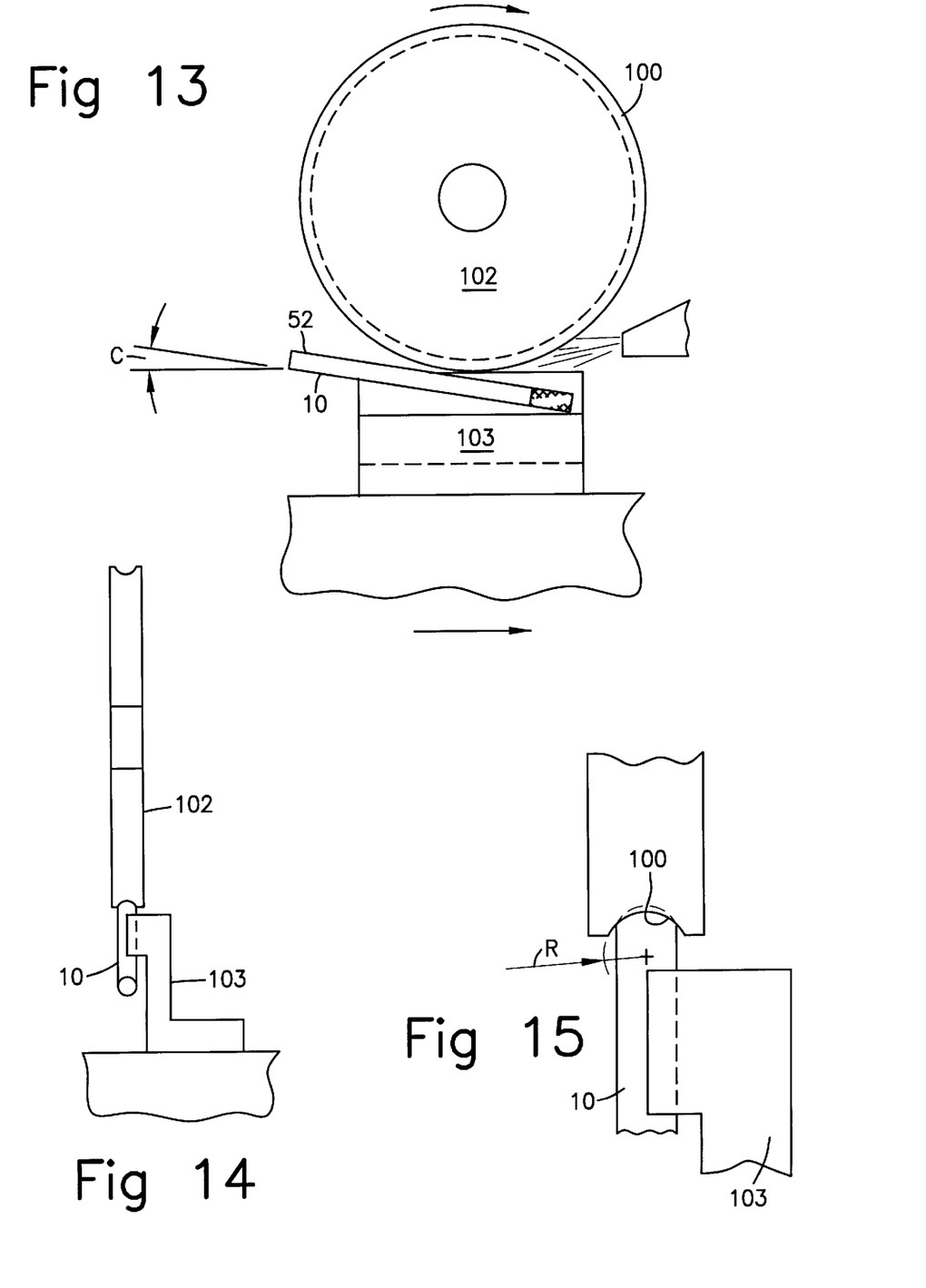
FIG. 13 is a diagrammatic elevational view of an electrochemical grinding apparatus used in a preferred method of producing the invention shown in FIG. 1.
FIG. 14 is a side view of FIG. 13.
FIG. 15 is an enlarged view of a portion of FIG. 14.
Figure 16:
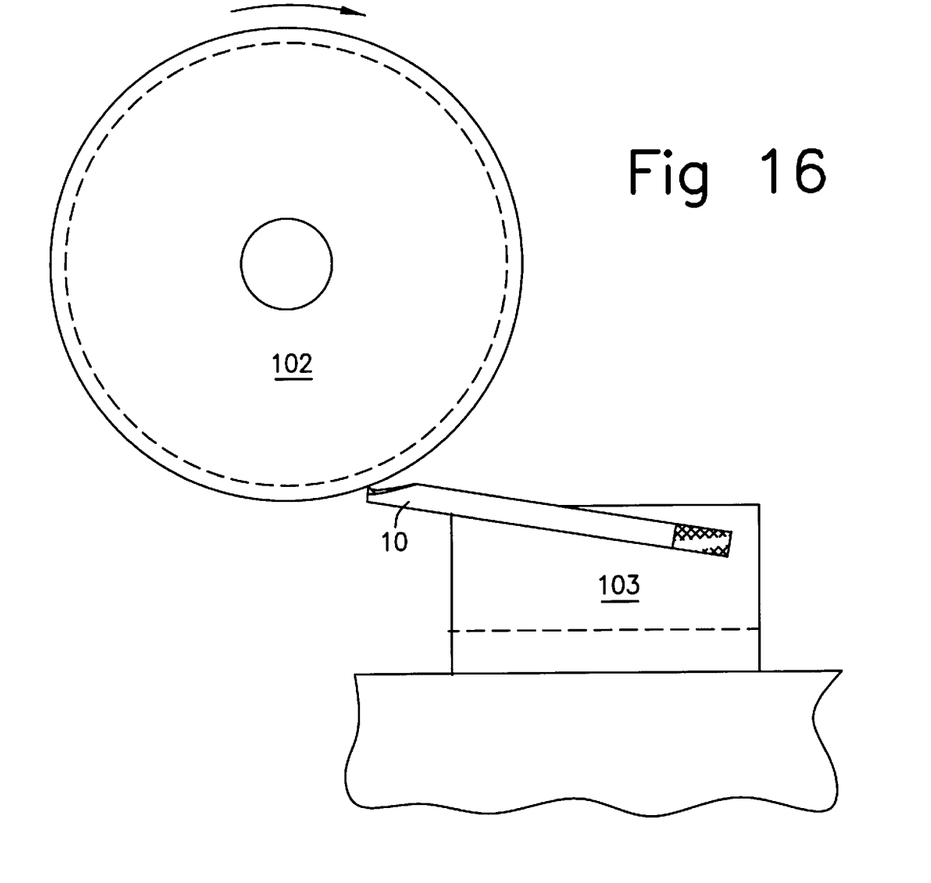
FIG. 16 is a view of FIG. 13 taken at another stage of the method step shown in FIG. 13.
Figure 17:
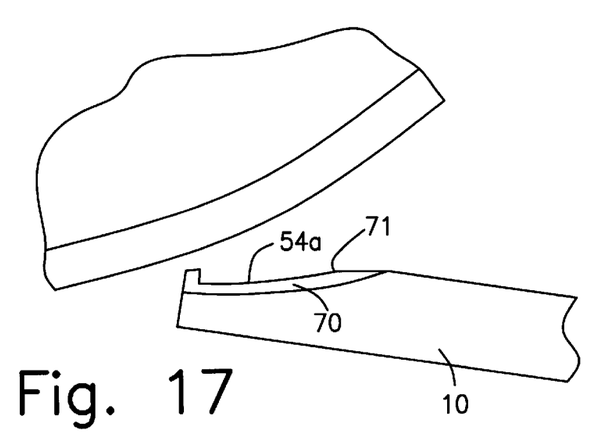
FIG. 17 is an enlarged view of a portion of FIG. 16.

The outer tube may be initially formed similarly to the inner member in that a flat circular cap (or machined shell) may be welded at its periphery to the open end of a cylindrical tube. The subsequent process is then performed in two stages: the first stage, shown in FIGS. 13–17, forms the primarily laterally facing portion 54a of window 54 and the second stage, shown in FIGS. 18–22, forms the primarily end facing portion 54b of window 54. While the stages may be performed in any order, the process generally begins with a closed cylindrical outer member, which will become outer member 10, being oriented in a fixture 103 in a predetermined orientation (at angle C) relative to a grinding wheel 102 having a concave rim 100 as shown in FIGS. 13–15. Movement of the tube relative to the wheel forms in the distal end 52 of the tube an arcuate surface having a radius of curvature equal to that of the radius of the surface formed in the rim 100 of the wheel 102. As the wheel passes entirely through the distal end of the tube as shown in FIGS. 16 and 17, an opening, i.e. window portion 54a, is created in the tube. Window portion 54a is thus formed with a peripheral land 70 angled at its proximal end 71, at an angle C relative to the axis of the outer tube.

Figures 18, 19, 20:
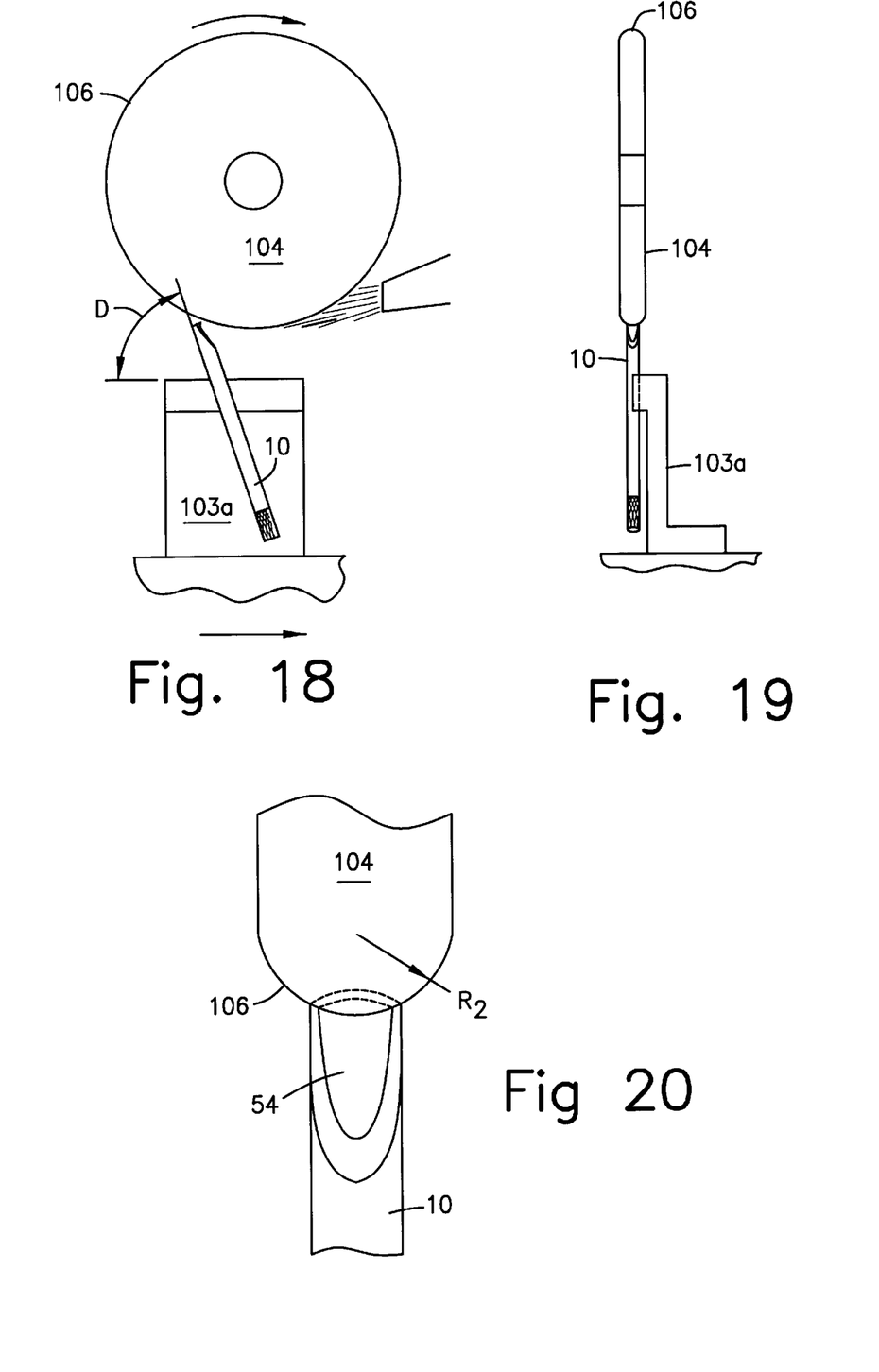
FIG. 18 is a diagrammatic view of an electrochemical grinding apparatus used in another stage of the preferred method of producing the invention shown in FIG. 1.
FIG. 19 is a side view of FIG. 18.
FIG. 20 is an enlarged view of a portion of FIG. 19.
Figure 21:
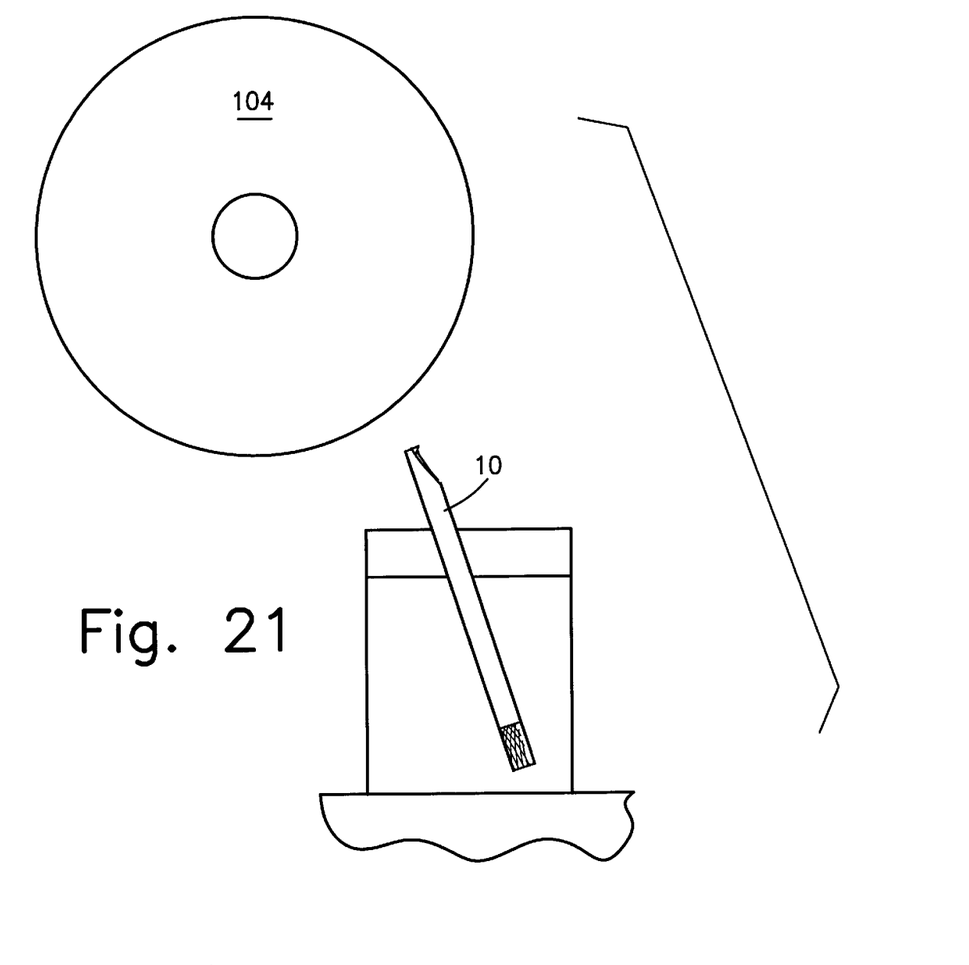
FIG. 21 is a view of FIG. 18 taken at a later stage of the method step shown in FIG. 18.

The second stage of the process is now used to form the end facing portion 54b of window 54. The partially formed outer tube member 10 shown in FIG. 17 is removed from the fixture used with wheel 102 and repositioned in a fixture 103a at an angle D relative to a grinding wheel 104 having a perimetral surface 106 as best seen in FIGS. 18–20. The convex radius of curvature of surface 106 is $R_2$ such that as the fixture 103a is moved tangentially relative to wheel 104, concave surface 57 is formed as best seen in FIG. 12.

The shape of the laterally facing portion 54a of window 54 and the proximal end of the surface of land 70 surrounding rim 58 may be considered as being defined by the locus of all points lying at the intersection of an elongated, transversely arcuate surface with the cylindrical body of the tube oriented at a predetermined angle C relative to the transversely arcuate surface. Put another way, the definition of the laterally facing land surface 70 bordering the perimeter of window 54 (as opposed to the end facing portion of the window) may be thought of as the intersection of a cylindrical body with an imaginary surface having a predetermined, symmetrical, concave arcuate profile which, in practice, is defined by the concave surface of the rim 100 of ECG wheel 102. Similarly, the definition of the end facing land surface 57 may be thought of as the intersection of an end wall 56 with another imaginary surface having a predetermined symmetrical convex arcuate profile.

Window 54 may be thought of as the intersection of a concave window portion 54b and a convex window portion 54a, the former produced at the distal end (end facing) of the tube by a convex forming tool and the latter produced at the distal end (lateral side) by a concave forming tool.

The various shapes of the land surfaces and edges incorporated into the embodiments may be easily varied and combined. For example, land 70 could be planar rather than arcuate, edge 56 could be straight or convex, edge 46 could be straight or convex, etc.

Figure 22:
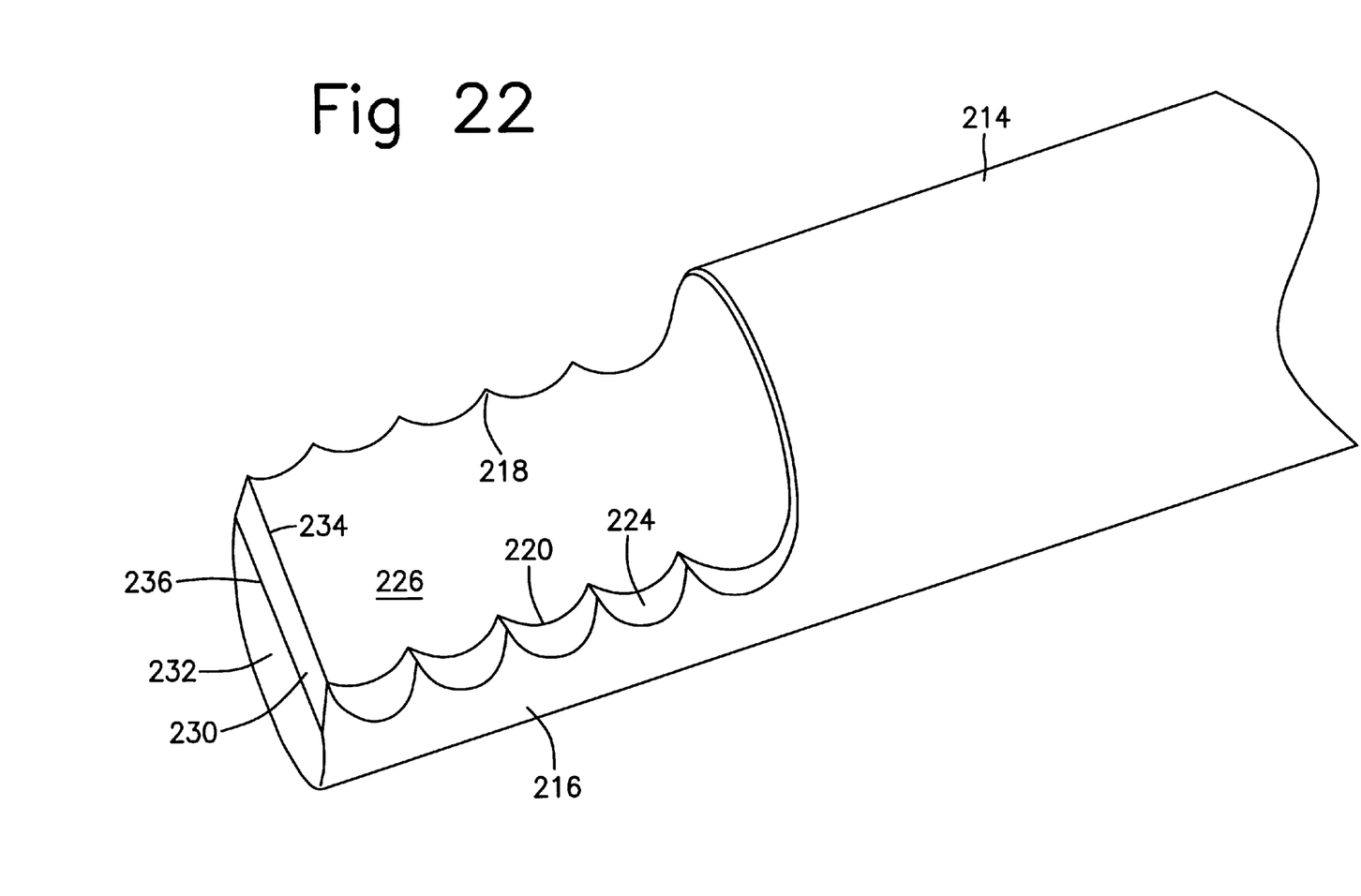
FIG. 22 is a front perspective view of the distal end of an alternate embodiment of the outer tubular member of a shaver blade assembly constructed in accordance with the principles of this invention.

An alternate embodiment of the outer tubular member 14 is shown in FIG. 22 as outer tubular member 214. Member 214 has a toothed distal end 216 and may be used in a shaver blade assembly (not shown) instead of member 14. The shaver blade assembly thus formed may have a toothed inner member as well as a toothed outer member or, if desired, the inner member may have a non-toothed cutting window. The tooth rows 218 and 220 of distal end 216 may be formed by the process described in the aforementioned U.S. Pat. No. 5,693,063 so that the outer surfaces adjacent the teeth of each row, e.g. outer surface 224 adjacent row 220, will be curved to produce a sharp edge at the intersection of the cylindrical inner surface 226 and each outer surface 224. The distal facing surface 230 of transverse wall 232 may be arcuate and convex, like surface 57, or may be a planar surface as shown. Surface 230 as shown extends transversely across the wall 232 and has two parallel edges 234 and 236. Edge 234 lies at the intersection of surface 230 with the proximally facing side of wall 232 and edge 236 lies at the intersection of surface 230 with the distally facing side of wall 232 which is perpendicular to the axis of tubular member 214.

It will be understood by those skilled in the art that numerous improvements and modifications may be made to the preferred embodiment of the invention disclosed herein without departing from the spirit and scope thereof.

What is claimed is:

1. A shaver blade assembly for resecting tissue comprising:

an elongated outer tubular member having an axis, a proximal end, a distal end, a laterally facing and end facing cutting window situated at said distal end, and further comprising a first transverse planar end wall at its distal end, said end wall having a distally facing outer surface, a proximally facing inner surface and a first transverse edge on its inner surface, said first transverse planar end wall joined with said distal end of said outer tubular member over a predetermined arcuate length of greater than 180° about the axis of said tubular member; and an elongated inner tubular member rotatably situated within said tubular outer member, said tubular inner member having a proximal end, a distal end, a laterally facing and end facing cutting window situated at said distal end, and further comprising a second transverse planar end wall at its distal end, said end wall having a distally facing outer surface, a proximally facing inner surface and a second transverse edge on its outer surface, said second transverse planar end wall joined with said distal end of said inner tubular member over a predetermined arcuate length of greater than 180° about the axis of said tubular member, said second transverse edge of said inner member adapted to cooperate with said first transverse edge of said outer member to resect tissue presented therebetween upon relative rotation of said inner and outer tubular members.

2. A shaver blade assembly according to claim 1 wherein at least one of said first and second transverse edges has a predetermined arcuate shape.

3. A shaver blade assembly according to claim 2 wherein at least a portion of said distally facing outer surface of said end wall of said outer member is a tapered surface, said portion and said proximally facing inner surface of said outer member intersecting to produce said first transverse edge.

4. A shaver blade assembly according to claim 3 wherein said tapered surface comprises the locus of points produced by the intersection of said first transverse end wall with a predetermined arcuate surface.

5. A shaver blade assembly according to claim 2 wherein at least one of said first and second transverse edges is provided with a point at at least one end thereof.

6. A shaver blade assembly according to claim 1 wherein said cutting window of said inner member comprises a longitudinally and transversely extending edge defining its perimeter.

7. A shaver blade assembly according to claim 6 wherein said longitudinally and transversely extending edge is provided with at least one tooth.

8. A shaver blade assembly according to claim 1 wherein said cutting window of said outer tubular member comprises a longitudinally and transversely extending edge defining its perimeter.

9. A shaver blade assembly according to claim 1 wherein at least said distal end of said outer tubular member comprises a tubular exterior surface which intersects with said distally facing outer surface of said end wall to form, in a plane perpendicular to said distally facing surface, a right angle between a line on said distally facing surface and a line on said tubular exterior surface.

* * * * *